United States Patent
Terasawa et al.

(10) Patent No.: US 9,829,787 B2
(45) Date of Patent: Nov. 28, 2017

(54) DEFECT INSPECTING METHOD, SORTING METHOD, AND PRODUCING METHOD FOR PHOTOMASK BLANK

(71) Applicant: SHIN-ETSU CHEMICAL CO., LTD., Tokyo (JP)

(72) Inventors: Tsuneo Terasawa, Joetsu (JP); Hiroshi Fukuda, Joetsu (JP); Takahiro Kishita, Joetsu (JP); Daisuke Iwai, Joetsu (JP); Atsushi Yokohata, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/181,691

(22) Filed: Jun. 14, 2016

(65) Prior Publication Data
US 2016/0377553 A1 Dec. 29, 2016

(30) Foreign Application Priority Data

Jun. 26, 2015 (JP) .................................. 2015-129006
May 24, 2016 (JP) .................................. 2016-102986

(51) Int. Cl.
*G03F 1/36* (2012.01)
*G03F 1/84* (2012.01)
*G01B 11/24* (2006.01)
*G01N 21/95* (2006.01)

(52) U.S. Cl.
CPC ............... *G03F 1/36* (2013.01); *G01B 11/24* (2013.01); *G01N 21/9501* (2013.01); *G03F 1/84* (2013.01); *G01N 2201/0638* (2013.01)

(58) Field of Classification Search
CPC ......... G03F 1/36; G03F 1/84; G01N 21/9501; G01B 11/24
USPC ........................................ 430/5, 30; 382/144
See application file for complete search history.

(56) References Cited

U.S. PATENT DOCUMENTS

| 6,617,603 | B2 | 9/2003 | Ishiguro et al. |
| 7,379,176 | B2 | 5/2008 | Sekine et al. |
| 7,630,068 | B2 * | 12/2009 | Tanaka .................. B82Y 10/00 250/372 |
| 2013/0336574 | A1 | 12/2013 | Nasser-Ghodsi et al. |

FOREIGN PATENT DOCUMENTS

| JP | 2001-174415 A | 6/2001 |
| JP | 2002-333313 A | 11/2002 |
| JP | 2005-265736 A | 9/2005 |
| JP | 2007-219130 A | 8/2007 |
| JP | 2013-19766 A | 1/2013 |

OTHER PUBLICATIONS

Extended European Search Report for European Application No. 16172622.9, dated Feb. 6, 2017.

* cited by examiner

*Primary Examiner* — Christopher G Young
(74) *Attorney, Agent, or Firm* — Birch, Stewart, Kolasch & Birch, LLP

(57) ABSTRACT

A method of inspecting a defect present at a surface portion of a photomask blank having at least one thin film formed on a substrate by use of the inspecting optical system. The method includes setting the distance between the defect and an objective lens of an inspecting optical system to a defocus distance, applying inspection light to the defect through the objective lens, collecting reflected light from the region irradiated with the inspection light, through the objective lens, as a magnified image, identifying a light intensity variation portion of the magnified image, and determining the rugged shape of the defect on the basis of a variation in light intensity of the light intensity variation portion of the magnified image.

15 Claims, 15 Drawing Sheets

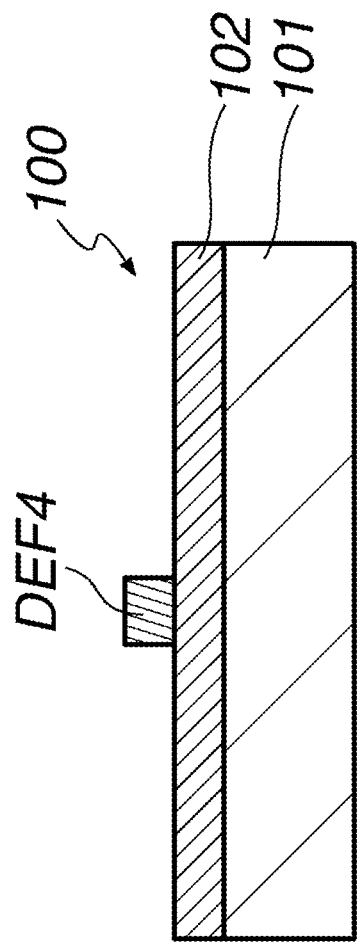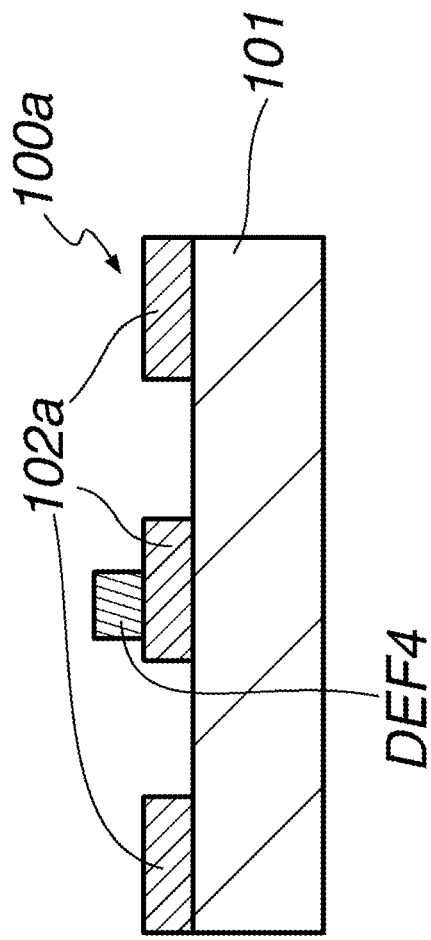

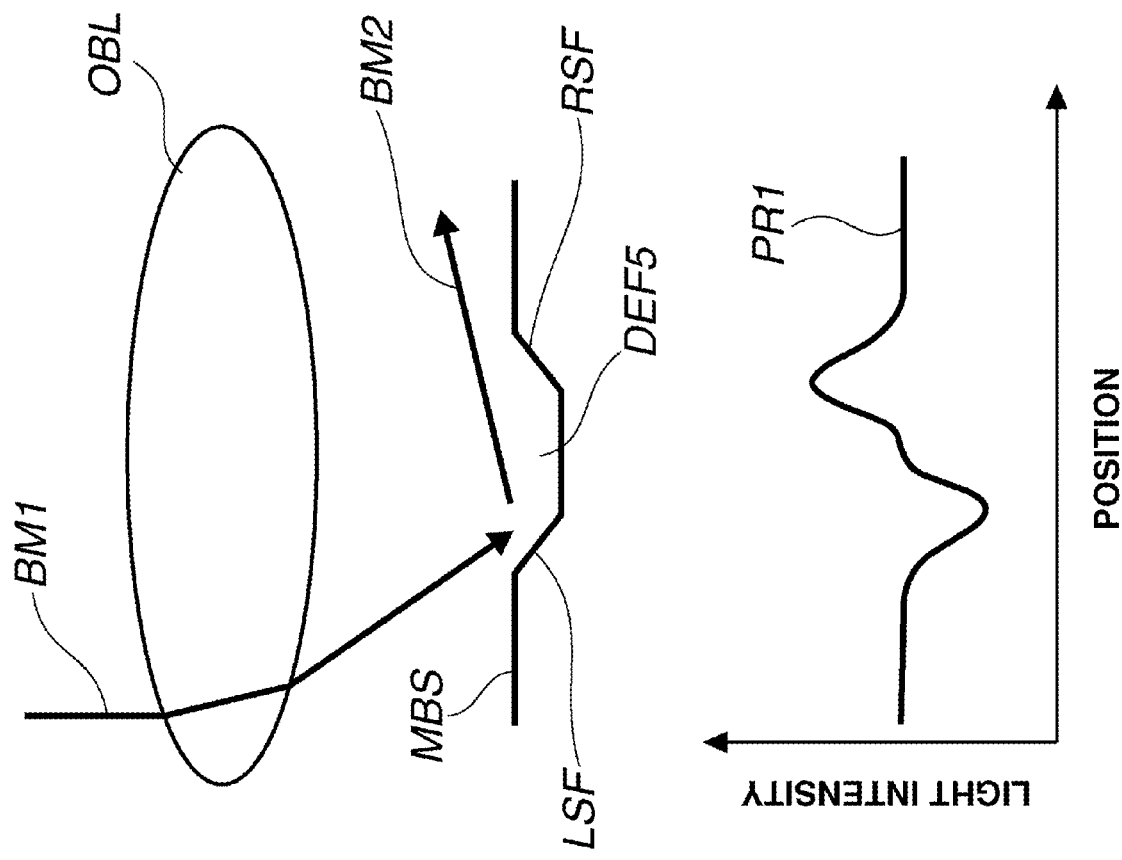

Δz = +200 nm

Δz = 0 nm

Δz = -200 nm

Δz = +200 nm

Δz = 0 nm

Δz = −200 nm

Δz = +200 nm

Δz = 0 nm

Δz = -200 nm

DEFECT INSPECTING METHOD, SORTING METHOD, AND PRODUCING METHOD FOR PHOTOMASK BLANK

CROSS-REFERENCE TO RELATED APPLICATION

This non-provisional application claims priority under 35 U.S.C. §119(a) to Patent Application No. 2015-129006, filed in Japan on Jun. 26, 2015,and Patent Application No.2016-102986, filed in Japan May 24, 2016, all of which are hereby expressly incorporated by reference into the present application.

TECHNICAL FIELD

The present invention relates to a defect inspecting method for a mask blank used for producing a photomask which, in turn, is used for manufacture of a semiconductor device or the like, particularly, to a defect inspecting method effective for determination of the rugged shape (projected/recessed shape) of a surface of a minute defect. Also, the present invention relates to a photomask blank sorting method and a photomask blank producing method based on the application of the defect inspecting method of the photomask blank.

BACKGROUND ART

Semiconductor devices are manufactured by repeating a photolithographic technique in which exposure light is applied to a mask (transfer mask) such as a photomask with a circuit pattern drawn thereon and the circuit pattern formed on the mask is transferred onto a semiconductor substrate (semiconductor wafer) through a demagnification optical system. The transfer mask is produced by forming the circuit pattern in a substrate (mask blank) formed with an optical thin film. Such an optical thin film is generally a thin film composed mainly of a transition metal compound or a thin film composed mainly of a transition metal-containing silicon compound. As the optical thin film, a film functioning as a light-shielding film or a film functioning as a phase shift film is selected according to the purpose.

The transfer mask such as photomask is for use as an original form for manufacturing semiconductor devices having minute patterns, and is demanded to be defect-free. This naturally leads to that the mask blank is also demanded to be free of defects. In addition, at the time of forming a circuit pattern, a resist film for processing is formed on a mask blank formed thereon with an optical thin film, and a final pattern is formed through an ordinary lithography step such as an electron beam lithography. Therefore, the resist film is also demanded to be free of defects such as pinholes. Under such circumstances, many investigations have been made as to the defect detecting technique for transfer masks and mask blanks.

JP-A 2001-174415 (hereinafter referred to as Patent Document 1) and JP-A 2002-333313 (hereinafter referred to as Patent Document 2) describe a method of applying laser light to a substrate to detect a defect and/or a foreign matter from scattered light, particularly a technology in which asymmetry is imparted to detection signals to determine whether a defect in question is a bump defect or a pit defect. In addition, JP-A 2005-265736 (hereinafter referred to as Patent Document 3) describes a technology in which deep ultraviolet (DUV) light conventionally used for general optical mask pattern inspection is used as inspection light. Further, JP-A 2013-19766 (hereinafter referred to as Patent Document 4) describes a technology in which inspection light is used for scanning in the state of being divided into a plurality of spots and reflected beams are received individually by light detection elements. On the other hand, JP-A 2007-219130 (hereinafter referred to as Patent Document 5) discloses a technology in which extreme ultraviolet (EUV) light having a wavelength of around 13.5 nm is used as inspection light to distinguish whether a defect in an EUV mask blank is a pit defect or a bump defect.

CITATION LIST

Patent Document 1: JP-A 2001-174415
Patent Document 2: JP-A 2002-333313
Patent Document 3: JP-A 2005-265736
Patent Document 4: JP-A 2013-19766
Patent Document 5: JP-A 2007-219130

DISCLOSURE OF INVENTION

Attendant on the continued miniaturization of semiconductor devices, argon fluoride (ArF) lithography technique using ArF excimer laser light of a wavelength of 193 nm has been frequently used. In addition, a technology in which a process called multi-patterning consisting in combining an exposure process and a processing process multiple times is adopted to finally form a pattern with a sufficiently fine size as compared to the exposure wavelength has been vigorously investigated. As aforementioned, a transfer mask is used as an original form of fine patterns and, therefore, defects on the transfer mask that would hinder fidelity of pattern transfer must all be excluded. Accordingly, in the mask blank production process, also, those defects which obstruct mask pattern formation should all be detected.

In transfer masks, a pit defect, particularly a pinhole defect, is fatal to mask pattern formation. On the other hand, a bump defect may not necessarily be fatal to mask pattern formation, though depending on the height of the defect. Also, a bump defect due to a foreign matter adhered to a surface of a photomask will not be a fatal defect if it can be removed by cleaning. Therefore, exclusion of mask blanks having a defect while regarding all these bump defects as fatal defects leads to a lowering in the yield. Accordingly, in defect inspection, highly accurate discrimination of the rugged shapes of defects is very important for assured exclusion of mask blanks having a fatal defect and for securement of a good yield.

The inspection apparatuses described in Patent Documents 1 to 4 all adopt an optical defect detecting method. An optical defect detecting method is advantageous in that inspection of defects in a wide region can be performed in a comparatively short time and, by using a light source with a shorter wavelength, it becomes possible to accurately detect finer defects. In addition, the documents provide a method in which whether a defect in question is a pit defect or a bump defect can be determined from the positional relation of a bright portion and a dark portion of detection signals obtained by an inspecting optical system using oblique illumination and/or a spatial filter. Further, Patent Document 5 describes a method for discriminating whether a phase defect is a pit defect or a bump defect, although the inspection object in this case is limited to EUV mask blank.

However, actual inspection experiments based on the inspection apparatuses described in Patent Documents 1 to 4 revealed that those defects which are determined to be pit defects on the basis of the positional relation of a bright portion and a dark portion of inspection signals obtained from a photomask blank may include bump defects, as confirmed by actual image observation of the defects by use of an atomic force microscope or an electron microscope. In other words, the inspection apparatuses described in Patent Documents 1 to 4 do not necessarily make it possible to accurately discriminate the rugged shapes of defects. Besides, the method described in Patent Document 5 is a method which is applicable to phase defects intrinsic of EUV mask blanks but is not easily applicable to currently mainstream photomask blanks associated with the use of krypton fluoride (KrF) excimer laser, ArF excimer laser, $F_2$ laser or the like. Accordingly, there has been a demand for establishment of a technique by which defects on photomask blanks can be accurately inspected without erroneous determination of a bump defect to be a pit defect, unlike in the cases of the conventional techniques.

Accordingly, an object of the present invention is to provide a defect inspecting method by which the rugged shapes of defects on a photomask blank can be highly reliably discriminated without erroneous determination of a bump defect to be a pit defect, and a photomask blank sorting method and a photomask blank producing method based on the application of the defect inspecting method.

As aforementioned, the related-art methods for discriminating the rugged shapes of defects on the basis of the positional relation of a bright portion and a dark portion of an inspection image had the following problem. Although pit defects such as pinholes formed in a thin film of a photomask blank are correctly determined to be pit defects, a bump defect due to adhesion of a foreign matter such as a particle of a material different from the material of the thin film to the surface of the thin film or a bump defect due to partial embedding of such a foreign matter into the thin film may sometimes be erroneously determined to be a pit defect.

The present inventors have studied in order to solve the above problems. As a result, the inventors found that when the defects detected to be pit defects by the related-art methods in the focus condition are subjected to collection of inspection images of the defects in the so-called defocus condition (where the focal position of the inspecting optical system is deviated from that in the focus condition) and the inspection images are subjected to evaluation of light intensity distribution, particularly to evaluation of the positional relation of a bright portion and a dark portion or the difference in light intensity between the bright portion and the dark portion, discrimination between true pit defects and bump defects can be achieved in regard of those defects which have been determined to be pit defects under the focus condition.

Therefore, the present invention provides the following defect inspecting method, sorting method, and producing method for a photomask blank.

In an aspect of the present invention, a method of inspecting a defect present at a surface portion of a photomask blank having at least one thin film formed on a substrate, by use of an inspecting optical system, includes:

(A1) a step of bringing the defect and an objective lens of the inspecting optical system close to each other, setting a distance between the defect and the objective lens to a focus distance, and, with the focus distance thus set, applying inspection light to the defect through the objective lens;

(A2) a step of collecting reflected light from a region irradiated with the inspection light, through the objective lens, as a first magnified image of the region;

(A3) a first determination step of identifying a light intensity variation portion of the first magnified image and determining a rugged shape of the defect on the basis of a variation in light intensity of the light intensity variation portion of the first magnified image;

(B1) a step of setting the distance between the defect and the objective lens of the inspecting optical system to a defocus distance deviated from the focus distance, and, with the defocus distance thus set, applying the inspection light to the defect through the objective lens;

(B2) a step of collecting reflected light from a region irradiated with the inspection light, through the objective lens, as a second magnified image of the region; and (B3) a second determination step of identifying a light intensity variation portion of the second magnified image and re-determining the rugged shape of the defect on the basis of a variation in light intensity of the light intensity variation portion of the second magnified image.

In the step (B3) of the above defect inspecting method, preferably, the rugged shape of the defect to be inspected is re-determined by comparison between a light intensity variation of a light intensity variation portion of a true pit defect that is preliminarily obtained by simulation and the light intensity variation of the light intensity variation portion of the second magnified image.

In the above defect inspecting method, the inspection light may be light having a wavelength of 210 nm to 550 nm.

In both the step (A1) and the step (B1), preferably, the application of the inspection light is conducted by oblique illumination in which optical axis of the inspection light is oblique in relation to a surface of the photomask blank.

In both the step (A2) and the step (B2), preferably, a spatial filter for shielding part of the reflected light is provided on an optical path of the reflected light, and the reflected light is collected through the spatial filter.

In in the step (A1), preferably, the photomask blank is placed on a stage that can be moved in an in-plane direction of the photomask blank, and the stage is moved in the in-plane direction to thereby bring the defect and the objective lens of the inspecting optical system close to each other.

In the defect inspecting method, when defect shape is determined to be a recessed shape in the first determination step, preferably, the steps (B1) to (B3) are carried out to re-determine the rugged shape of the defect.

In another aspect of the present invention, a method of sorting a photomask blank includes sorting out a photomask blank having no pit defect from the photomask blanks subjected to the steps (B1) to (B3), on the basis of the rugged shape of the defect re-determined in the second determination step of the aforementioned defect inspecting method.

In a further aspect of the present invention, a method of producing a photomask blank includes:

a step of forming at least one thin film on a substrate; and a step of determining rugged shape of a defect present in the thin film by the aforementioned defect inspecting method.

ADVANTAGEOUS EFFECTS OF THE INVENTION

According to the described aspects of the present invention, defects of a photomask blank can be inspected while highly reliably discriminating the rugged shapes of the defects, while using an optical defect inspecting method. In addition, by application of the defect inspecting method, photomask blanks having a pit defect, a fatal defect, can be assuredly excluded, without erroneously determining a bump defect to be a pit defect. Accordingly, photomask blanks having no fatal defect can be provided at a lower cost and in a high yield.

BRIEF DESCRIPTION OF THE DRAWINGS

FIGS. 2A to 2C are sectional views in which a pit defect is present in a photomask blank, wherein FIGS. 2A and 2B depict a photomask blank having a pit defect, and FIG. 2C depicts a photomask produced from the photomask blank having the pit defect.

FIGS. 3A and 3B are sectional views in which a bump defect is present on a photomask blank, wherein FIG. 3A depicts a photomask blank having a bump defect, and FIG. 3B depicts a photomask produced from the photomask blank having the bump defect.

FIG. 5A is a conceptual diagram depicting a mode of reflected light relevant to inspection light applied to a pit defect in a photomask blank by oblique illumination, and FIG. 5B depicts a sectional profile of light intensity distribution of an inspection image.

DESCRIPTION OF THE PREFERRED EMBODIMENTS

In the first place, steps for producing a photomask from a photomask blank will be described. FIGS. 1A to 1F illustrate an example of the steps for producing a photomask from a photomask blank, and are sectional views of the photomask blank, an intermediate product or the photomask at each stage of the production step. In the photomask blank, at least one thin film such as optical thin film or processing aid thin film is formed on a transparent substrate.

Figure 1A:
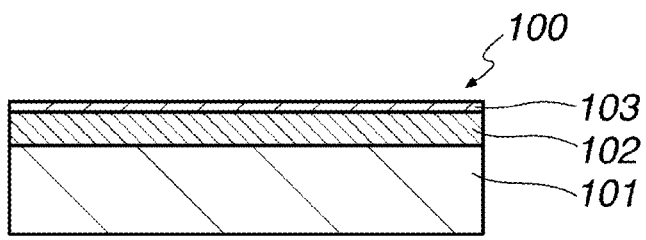
FIGS. 1A to 1F are sectional views for illustrating an outline of steps for producing a photomask from a photomask blank, depicting each stage of the production step.
Figure 1B:
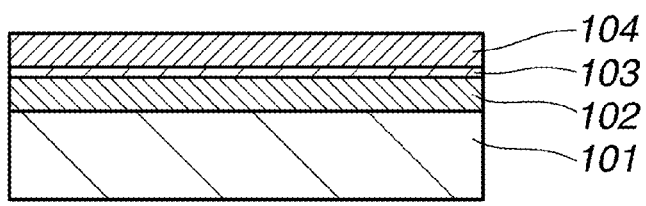
Figure 1C:
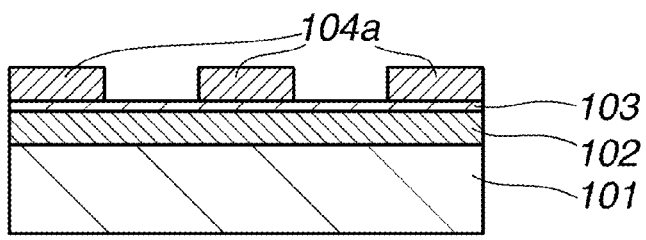
Figure 1D:
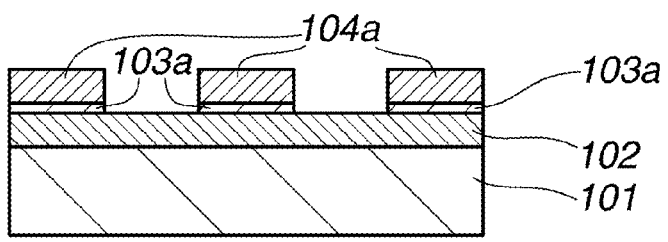
Figure 1E:
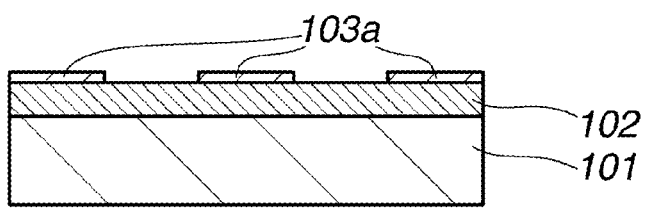
Figure 1F:
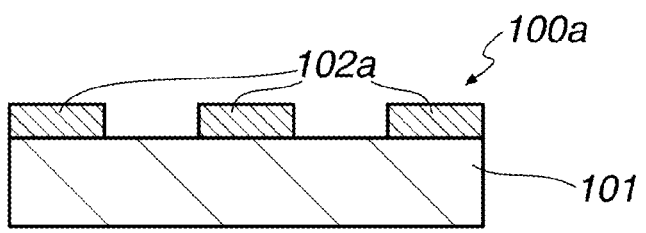

In a photomask blank 100 depicted in FIG. 1A, an optical thin film 102 functioning as a light-shielding film, a phase shift film such as a halftone phase shift film or the like is formed on a transparent substrate 101, and a hard mask film (processing aid thin film) 103 is formed on the optical thin film 102. In producing a photomask from such a photomask blank, first, a resist film 104 for processing of the hard mask film 103 is formed on the hard mask film 103 (FIG. 1B). Next, through a lithographic step by electron beam lithography or the like, a resist pattern 104a is formed from the resist film 104 (FIG. 1C), then with the resist pattern 104a as an etching mask, the underlying hard mask film 103 is processed to form a hard mask film pattern 103a (FIG. 1D), and the resist pattern 104a is removed (FIG. 1E). Further, with the hard mask film pattern 103a as an etching mask, the underlying optical thin film 102 is processed to form an optical thin film pattern 102a, and thereafter the hard mask film pattern 103a is removed, thereby a photomask 103 is obtained (FIG. 1F).

Figure 2A:
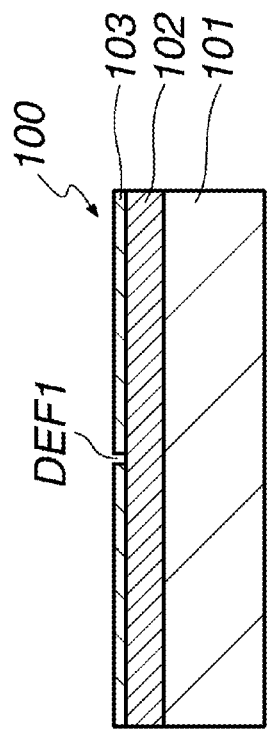
Figure 2B:
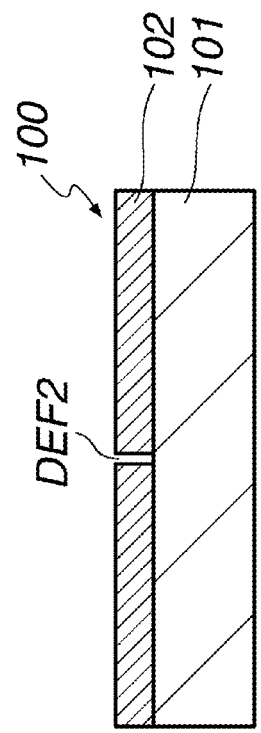
Figure 2C:
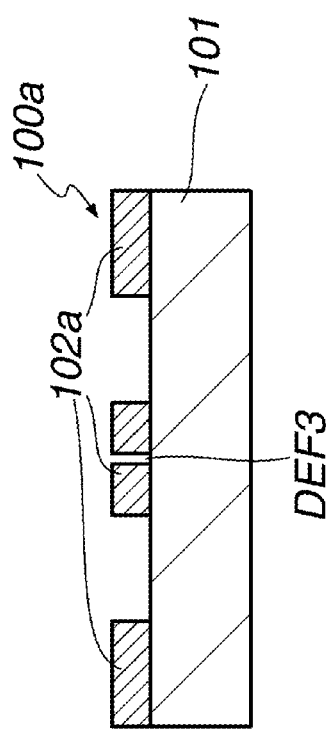

When a pit defect such as a pinhole defect is present in a thin film of a photomask blank, it finally causes a defect in a mask pattern on the photomask. A typical example of a pit defect in a photomask blank is depicted in FIGS. 2A to 2C. FIG. 2A is a sectional view depicting an example of a photomask blank 100 having a pit defect DEFT in a hard mask film 103 formed on an optical thin film 102 on a transparent substrate 101 in order to perform accurate processing of the optical thin film 102, whereas FIG. 2B is a sectional view depicting an example of a photomask blank 100 having a pit defect DEF2 in an optical thin film 102 itself formed on a transparent substrate 101.

In either of the photomask blanks, if a photomask is produced from such a photomask blank by the production steps illustrated in FIGS. 1A to 1F, there results a photomask wherein a pit defect DEF3 arising from the photomask blank is present in an optical thin film 102a, as represented by a photomask 100a depicted in FIG. 2C. Then, this pit defect DEF3 causes a pattern transfer error in exposure conducted using the photomask. Therefore, in regard of such a pit defect in a photomask blank, it is necessary to detect the defect before processing the photomask blank and to exclude photomask blanks having such a defect or to correct such defects.

On the other hand, FIGS. 3A and 3B illustrate a case where a bump defect such as a particle defect is present on a photomask blank. FIG. 3A is a sectional view depicting an example of a photomask blank 100 having a bump defect DEF4 present on an optical thin film 102 formed on a transparent substrate 101. If a photomask is produced from such a photomask blank by the production steps as depicted in FIGS. 1A to 1F, there results a photomask wherein the bump defect DEF4 is left on an optical thin film pattern 102a, as represented by a photomask 100a depicted in FIG. 3B. However, a bump defect may not be a fatal defect, depending on the defect size; in addition, a bump defect due to a foreign matter adhered to a surface of a photomask will not be a fatal defect if it can be removed by cleaning.

In this way, whether a defect present on a photomask blank is a pit defect such as pinhole that is a fatal defect or is a bump defect that is often not a fatal defect will be an important factor concerning the guarantee of photomask blank quality and the yield in photomask blank production. Therefore, it is desirable to provide a method by which the rugged shapes of defects can be highly reliably discriminated using by optical techniques.

Figure 4:
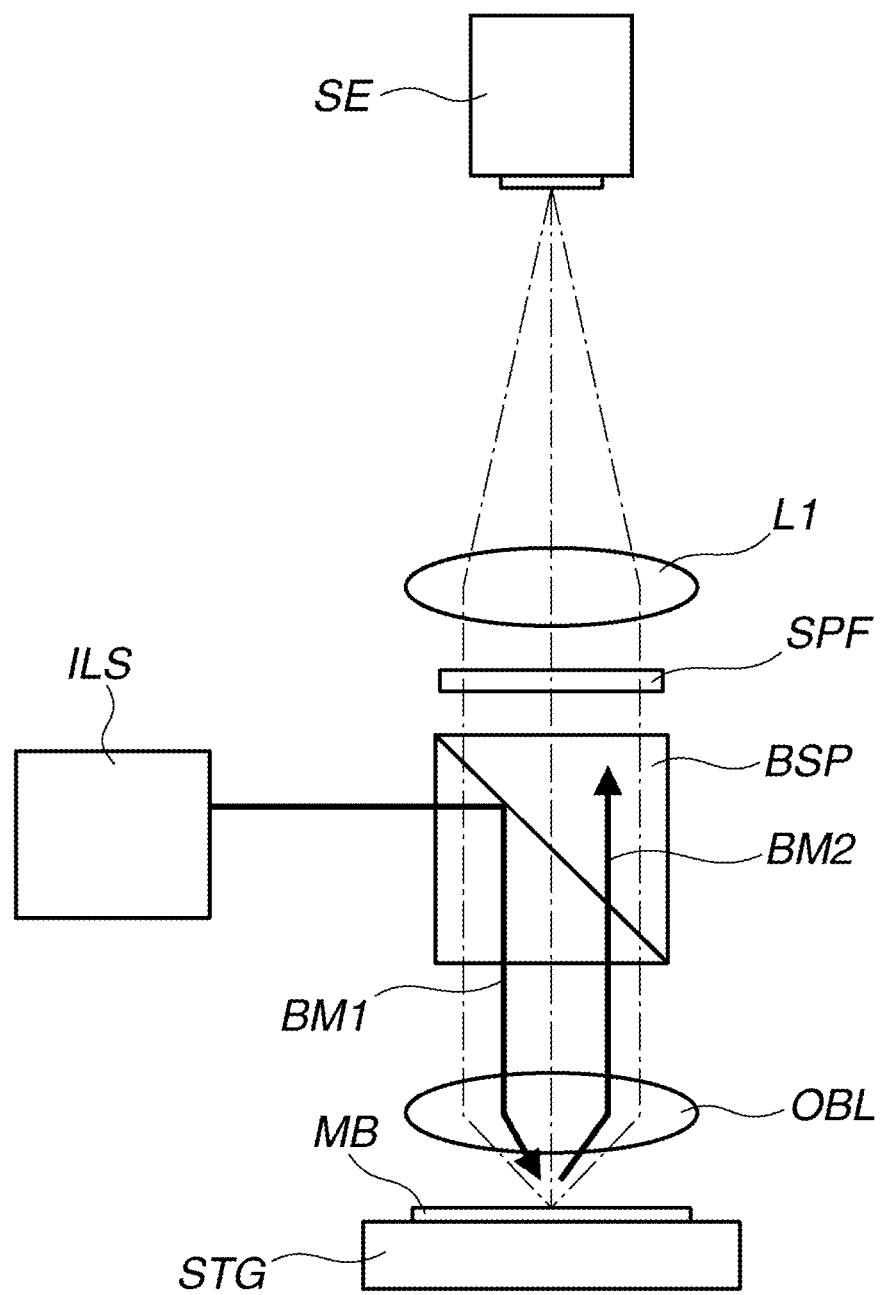
FIG. 4 illustrates the configuration of an inspecting optical system for use in defect inspection of a photomask blank.

In the next place, an inspecting optical system preferably used for defect inspection of a photomask blank, specifically, an inspecting optical system preferably used for determining the rugged shape of a defect at a surface portion of a photomask blank will be described. FIG. 4 is a conceptual diagram depicting an example of basic configuration of an inspecting optical system, which includes a light source ILS, a beam splitter BSP, an objective lens OBL, a stage STG which can be moved with a photomask blank MB mounted thereon, and an image detector SE. The light source ILS is configured to be able to emit light of a wavelength of approximately 210 nm to 550 nm, and inspection light BM1 emitted from the light source ILS is deflected by the beam splitter BSP, to be applied to a predetermined region of the photomask blank MB through the objective lens OBL. Reflected light BM2 from a surface of the photomask blank MB is collected by the objective lens OBL, and passes through the beam splitter BSP and a lens L1 to reach a light receiving surface of the image detector SE. In this case, the position of the image detector SE is controlled in such a manner that a magnified inspection image of the surface of the photomask blank MB is formed on the light receiving surface of the image detector SE. Then, data of the magnified inspection image collected at the image detector SE is subjected to image processing calculation, whereby calculation of defect size and determination of the rugged shape of the defect are conducted, and the results are recorded as defect information.

The magnified inspection image can be collected, for example, by a direct method in which a detector having a multiplicity of optical detection elements are arrayed as pixels such as a charge-coupled device (CCD) camera is used as the image detector SE, and a magnified image formed by the reflected light BM2 from the surface of the photomask blank MB through the objective lens OBL is collected as a two-dimensional image. Alternatively, a method may be adopted in which the surface of the photomask blank MB is scanned with the inspection light BM1 by scanning means, light intensity of the reflected light BM2 is sequentially collected by the image detector SE, the collected light is recorded through photoelectric conversion, and a two-dimensional image of the whole area of the photomask blank MB is produced. Further, a spatial filter SPF for shielding part of the reflected light BM2 may be disposed at a pupil position of the inspecting optical system, for example, on an optical path of the reflected light BM2, particularly between the beam splitter BSP and the lens L1. In this case, part of the optical path of the reflected light BM2 may be shielded as required, whereby a magnified inspection image can be trapped by the image detector SE. The incidence angle of the inspection light BM1 can be set to a predetermined angle in relation to the photomask blank MB. Note that positioning of the defect to be inspected may be conducted in such a manner that the defect as an inspection object can be observed through the objective lens OBL. In this case, the photomask blank MB is placed on the mask stage STG, and the photomask blank MB can be positioned such as to be observable through the objective lens OMB, by movement of the mask stage STG.

Now, referring to FIGS. 5A, 5B, 6A, and 6B, description will be made of a difference between an inspection image of a pit defect and an inspection image of a bump defect in the case where the distance between a defect and the objective lens of the inspecting optical system is set to a focus distance and reflected light is collected in this condition. FIG. 5A is a conceptual diagram depicting an example in which inspection light BM1 from the inspecting optical system depicted in FIG. 4 is applied to a surface MBS of a photomask blank having a typical pit defect DEF5 obliquely from a left side. Such oblique illumination can be realized, for example, by a method wherein the position of the inspection light BM1 emitted to the photomask blank MB from the light source ILS depicted in FIG. 4 is controlled by controlling the position of aperture (located between the light source ILS and the beam splitter BSP). In this case, the reflected light BM2 reflected on a side surface LSF on the left side of the pit defect DEF5 in the figure is concentrated on the right side relative to the objective lens OBL by regular reflection and, hence, is not sufficiently taken into the objective lens OBL. On the other hand, the reflected light reflected on a side surface RSF on the right side of the pit defect DEF5 in the figure is sufficiently taken into the objective lens OBL through regular reflection. As a result, the light intensity distribution of an inspection image obtained at the image detector SE assumes a sectional profile PR1 as depicted in FIG. 5B, wherein the left side of the pit defect DEF5 is a dark portion and the right side is a bright portion.

Figures 6A, 6B:
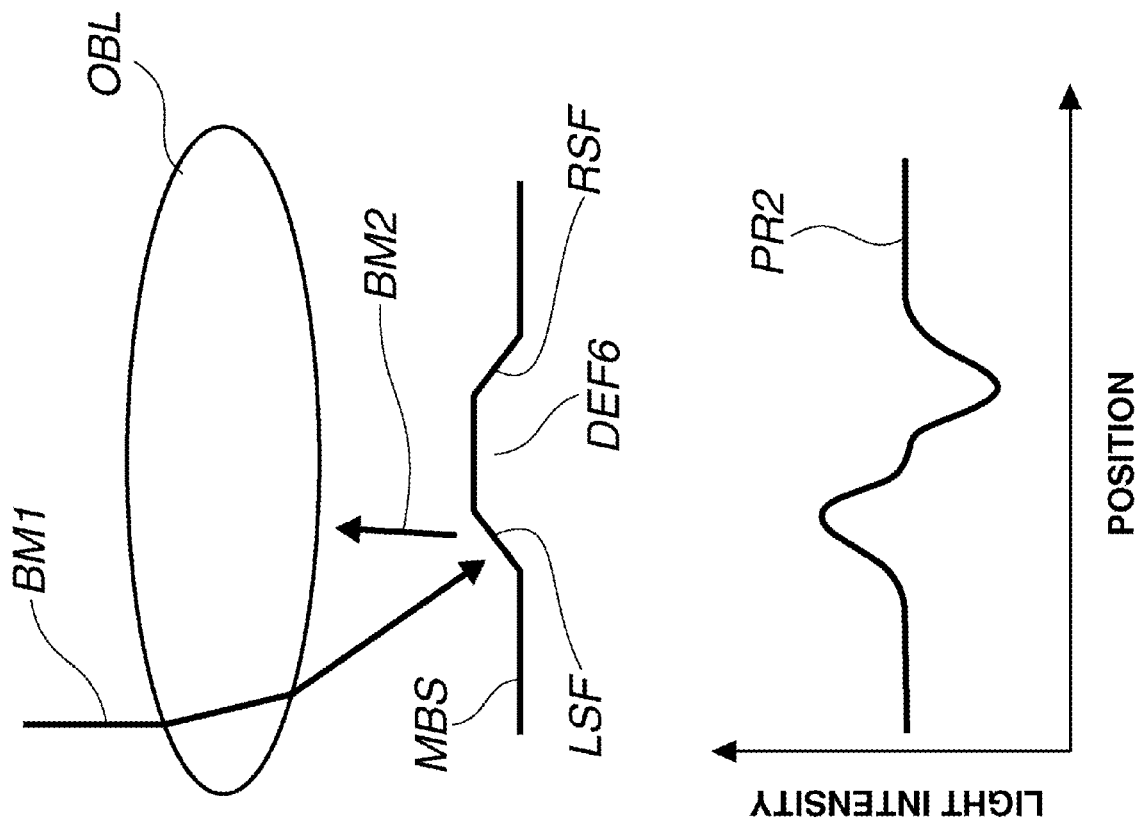
FIG. 6A is a conceptual diagram depicting a mode of reflected light relevant to inspection light applied to a bump defect on a photomask blank by oblique illumination.
FIG. 6B depicts a sectional profile of light intensity distribution of an inspection image.

On the other hand, FIG. 6A is a conceptual diagram depicting an example in which inspection light BM1 from the inspecting optical system depicted in FIG. 4 is applied to a surface MBS of a photomask blank having a typical bump defect DEF6 obliquely from a left side. In this case, the reflected light BM2 reflected on a side surface LSF on the left side of the bump defect DEF6 in the figure is sufficiently taken into the objective lens OBL through regular reflection. On the other hand, the reflected light reflected on a side surface RSF on the right side of the bump defect DEF6 in the figure is concentrated on the right side relative to the objective lens OBL by regular reflection and, hence, is not sufficiently taken into the objective lens OBL. As a result, the light intensity distribution of the inspection image obtained at the image detector SE assumes a sectional profile PR2 as depicted in FIG. 6B, wherein the left side of the bump defect DEF6 is a bright portion and the right side is a dark portion.

In this way, by application of oblique illumination, the rugged shape of a defect can be determined from the positional relation of bright and dark portions of the inspection image obtained. While an example of oblique illumination from a left side in the figure has been depicted in FIGS. 5A to 6B, the illumination direction can be set arbitrarily, and taking the inspection light incidence side as a reference in the inspection image obtained, the rugged shape of a defect can be similarly determined from the positional relation between bright and dark portions of the inspection image or the difference in light intensity between the bright and dark portions.

In addition, in the case of a configuration wherein a spatial filter SPF for shielding part of the reflected light is provided on an optical path of the reflected light in an inspecting optical system and the reflected light is collected through the spatial filter SPF as depicted in FIG. 4, illumination of the surface of the photomask blank from a perpendicular (normal) direction can also generate bright and dark portions of an inspection image, like in the case of the aforementioned oblique illumination. In this case, for example, when one half of the optical path of the reflected light is shielded and the inspection light incidence side is taken as a reference, the rugged shape of a defect can be determined from the positional relation between the bright and dark portions of the inspection image or the difference in light intensity between the bright and dark portions.

Figure 7A:
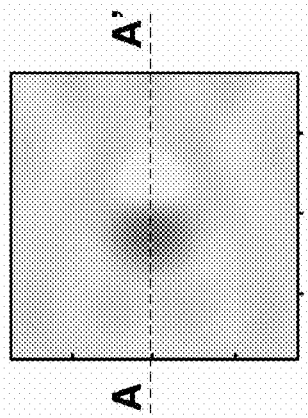
FIG. 7A is a plan view of a photomask blank having a bump defect wherein part of a foreign matter formed of a material with a low refractive index is projected from an optical thin film.

In the case where a foreign matter such as a particle is embedded in an optical thin film and part of the foreign matter is projected from the optical thin film to constitute a bump defect at a surface portion of a photomask blank or the like cases, however, it may sometimes be impossible to accurately detect whether the defect is a pit defect or a bump defect on the basis of only the aforementioned positional relation of the bright and dark portions of the inspection image. FIGS. 7A and 7B are respectively a plan view and a sectional view of a photomask blank 100 having such a bump defect (first mode). These figures depict a state in which a foreign matter of a material lower in refractive index than an optical thin film 102 of a molybdenum silicide (MoSi) material formed on a quartz substrate 101 transparent to inspection light is present at a surface portion of the optical thin film 102 as a bump defect DEF7.

Figure 7C:
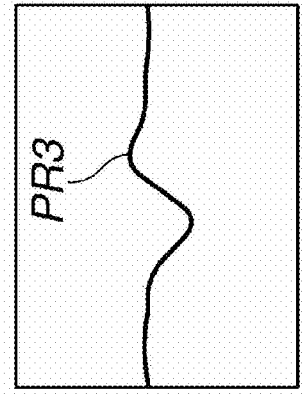
FIG. 7C is an inspection image of the bump defect.
Figure 7B:
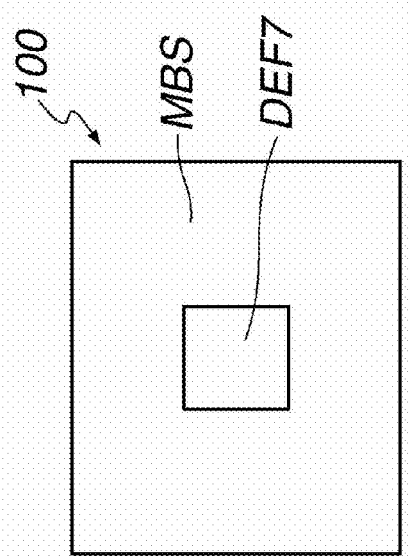
FIG. 7B is a sectional view of the photomask blank.
Figure 7D:
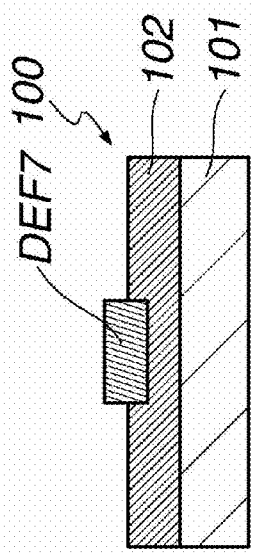
FIG. 7D depicts a sectional profile of light intensity distribution of an inspection image.

In the case where the distance between a defect and the objective lens of the inspecting optical system is set to a focus distance and the surface MBS of the photomask blank having the bump defect DEF7 is irradiated with inspection light from a left side in the figure by oblique illumination and the reflected light is collected by use of the inspecting optical system depicted in FIG. 4, like in the case of the pit defect depicted in FIGS. 5A and 5B or the bump defect depicted in FIGS. 6A and 6B, an inspection image with a light intensity distribution depicted in FIG. 7C is obtained. In addition, the light intensity distribution in a section along line A-A' in FIG. 7C assumes a profile PR3 as depicted in FIG. 7D. In this case, comparison of the result with those in the cases depicted in FIGS. 5A and 5B and FIGS. 6A and 6B would lead to a determination that the defect in question is a pit defect, but actually the defect is a bump defect.

However, it has been found that in the case where the distance between a defect and the objective lens of the inspecting optical system is set to a defocus distance deviated from the focus distance and the reflected light is collected, for a bump defect that might be determined to be a pit defect like the one depicted in FIGS. 7A and 7B and a true pit defect, there is a difference between the bump defect and the true pit defect in inspection image and light intensity distribution in the condition where the defocus distance is set (namely, in the defocused condition).

Figure 8A:
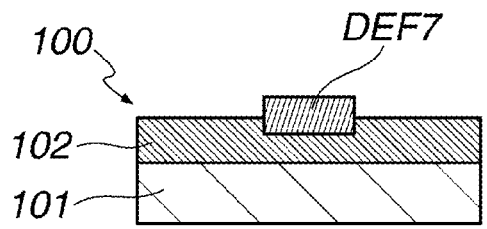
FIG. 8A is a sectional view of a photomask blank having a bump defect wherein part of a foreign matter is projected from an optical thin film.
Figure 8B:
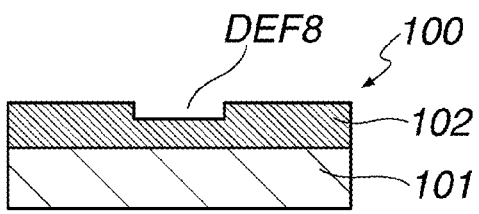
FIG. 8B is a sectional view of a photomask blank having a true pit defect.

FIG. 8A is a sectional view similar to FIG. 7B. On the other hand, FIG. 8B is a sectional view of a photomask blank 100 having a true pit defect DEF8 in an optical thin film 102 of an MoSi material formed on a quartz substrate 101 transparent to inspection light.

Figure 8C:
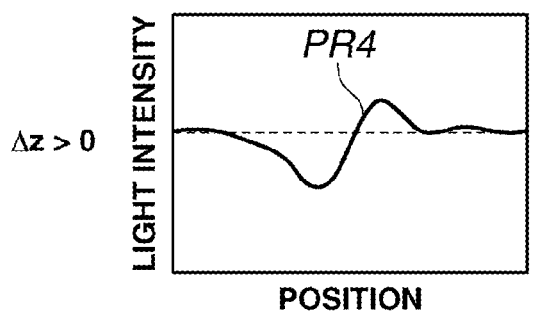
FIGS. 8C and 8D depict sectional profiles of light intensity distribution of inspection images of the respective defects in a positive defocus condition.
Figure 8D:
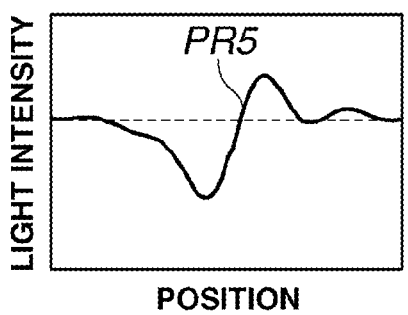
Figure 8E:
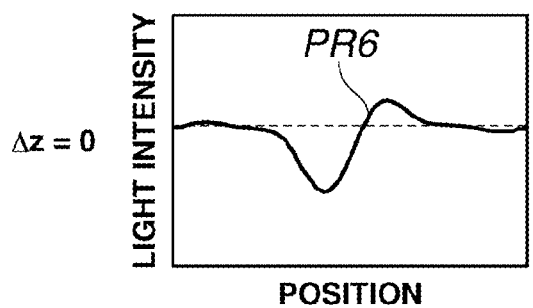
FIGS. 8E and 8F depict sectional profiles of light intensity distribution of inspection images of the respective defects in a focus condition.
Figure 8F:
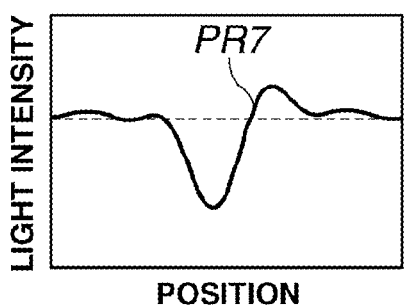
Figure 8G:
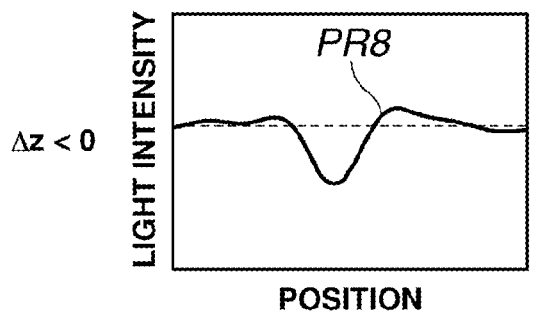
FIGS. 8G and 8H depict sectional profiles of light intensity distribution of inspection images of the respective defects in a negative defocus condition.
Figure 8H:
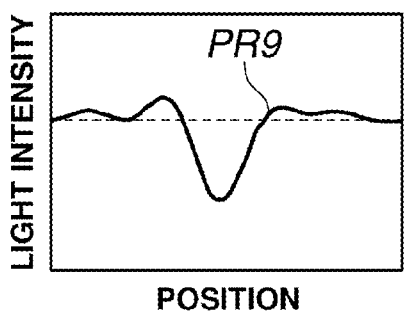

When the bump defect DEF7 and the pit defect DEF8 are subjected to irradiation of the surface of the photomask blank with inspection light from a left side in the figure by oblique illumination and the reflected light is collected by use of the inspecting optical system depicted in FIG. 4 like in the case of the pit defect depicted in FIGS. 5A and 5B or the bump defect depicted in FIGS. 6A and 6B, there is no difference in positional relation of the bright and dark portions between a sectional profile PR6 (FIG. 8E) of light intensity distribution of the bump defect DEF7 and a sectional profile PR7 (FIG. 8F) of light intensity distribution of the pit defect DEF8, in the case of a focused condition ($\Delta z=0$; Note that $\Delta z$ represents the difference from the focus distance) where the distance between the defect and the objective lens of the inspecting optical system is set to the focus distance. In addition, in the case of a positive defocus condition ($\Delta z>0$) where the distance between the defect and the objective lens of the inspecting optical system is set to a positive defocus distance, namely, set to be nearer than the focus distance by raising the mask stage STG with the photomask blank MB mounted thereon, also, there is no difference in positional relation of the bright and dark portions between a sectional profile PR4 (FIG. 8C) of light intensity distribution of the bump defect DEF7 and a sectional profile PR5 (FIG. 8D) of light intensity distribution of the pit defect DEF8. On the other hand, in the case of a negative defocus condition ($\Delta z$ 21 0) where the distance between the defect and the objective lens of the inspecting optical system is set to a negative defocus distance, namely, set to be farther than the focus distance by lowering the mask stage STG with the photomask blank MB mounted thereon, the positional relation of the bright and dark portions is reversed between a sectional profile PR8 (FIG. 8G) of light intensity distribution of the bump defect DEF7 and a sectional profile PR9 (FIG. 8H) of light intensity distribution of the pit defect DEF8.

Thus, based on the inspection image and the light intensity distribution obtained in the focus condition or the positive defocus condition, the bump defect DEF7 and the pit defect DEF8 would be determined to be of the same shape. Based on the inspection image and the light intensity distribution obtained in the negative defocus condition, however, the disposition of the bright and dark portions is reversed as the left side in the figure is the bright portion and the right side is the dark portion in the case of the pit defect DEF8 that is a true pit defect, whereas the disposition of the bright and dark portions is not reversed in the case of the bump defect DEF7 due to partial projection of a foreign matter from the optical thin film. The light intensity distribution of the bright and dark portions of the inspection image varies depending on the defect width, height, depth, and defocus amount and the like, but in any of the various cases, a difference in the positional relation of the bright and dark portions is generated between the pit defect DEF8 and the bump defect DEF7 under the negative defocus condition. By utilizing this difference obtained in the negative defocus condition, the defect that is actually a bump defect but would be determined to be a pit defect under the focus condition can be correctly determined to be a bump defect.

Figure 9A:
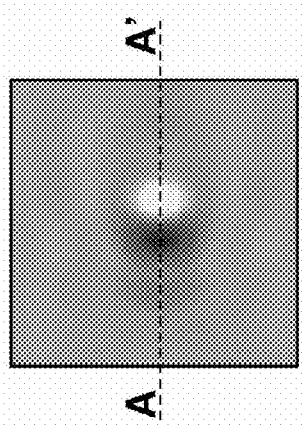
FIG. 9A is a plan view of a photomask blank having a bump defect due to by an adhered matter of a material substantially transparent to inspection light.
Figure 9C:
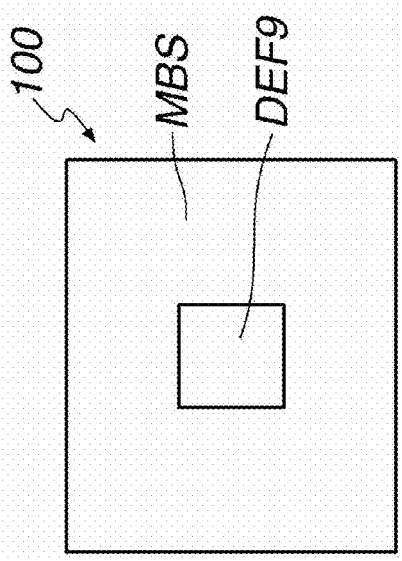
FIG. 9C is an inspection image of the bump defect.
Figure 9B:
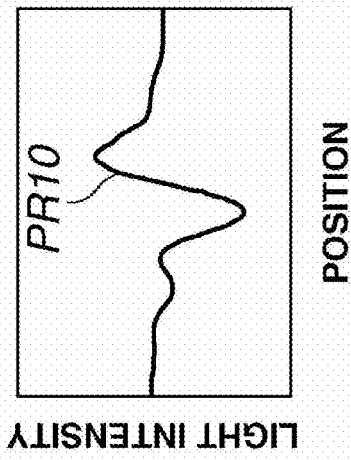
FIG. 9B is a sectional view of the photomask blank.
Figure 9D:
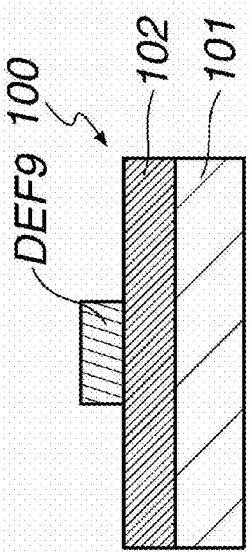
FIG. 9D depicts a sectional profile of light intensity distribution of the inspection image.

In the next place, description will be made of a case where an adhered matter of a material substantially transparent to inspection light is present as a defect as illustrated in FIGS. 9A to 9D. FIGS. 9A and 9B are respectively a plan view and a sectional view of a photomask blank 100 having such a bump defect (second mode). These figures depict a condition in which a bump defect DEF9 due to an adhered matter of a material substantially transparent to inspection light is present at a surface of the optical thin film 102 of an MoSi material formed on a quartz substrate 101 transparent to the inspection light. In this case, the optical thin film 102 itself is flat.

When the bump defect DEF9 is subjected to irradiation of the surface MBS of the photomask blank with inspection light from a left side in the figure by oblique illumination and the reflected light is collected by use of the inspecting optical system depicted in FIG. 4 like the pit defect depicted in FIGS. 5A and 5B or the bump defect depicted in FIGS. 6A and 6B while setting the distance between the defect and the objective lens of the inspecting optical system to a focus distance, an inspection image with a light intensity distribution depicted in FIG. 9C is obtained. The light intensity distribution in a section along line A-A' in FIG. 9C assumes a profile PR10 depicted in FIG. 9D. In this case, comparison of this result with those in the cases depicted in FIGS. 5A and 5B and FIGS. 6A and 6B would lead to a determination that the defect in question is a pit defect, but the defect is actually a bump defect.

However, it has been found that in the case where the distance between a defect and the objective lens of the inspecting optical system is set to a defocus distance deviated from the focus distance and the reflected light is collected, for a bump defect that might be determined to be a pit defect like the one depicted in FIGS. 9A and 9B and a true pit defect, there is a difference between the bump defect and the true pit defect in inspection image and light intensity distribution in the condition where the defocus distance is set (namely, in the defocused condition).

Figure 10A:
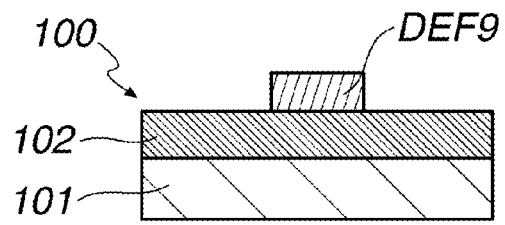
FIG. 10A is a sectional view of a photomask blank having a bump defect due to an adhered matter of a material substantially transparent to inspection light.

FIG. 10A is a sectional view similar to FIG. 9B. On the other hand, a sectional view of a photomask blank 100 having a true pit defect DEF8 is depicted in FIG. 8B.

Figure 10B:
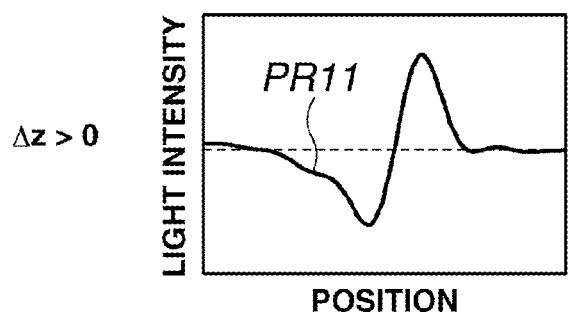
FIGS. 10B to 10D depict sectional profiles of light intensity distribution of inspection images of the bump defect in a positive defocus condition, a focus condition, and a negative defocus condition, respectively.
Figure 10C:
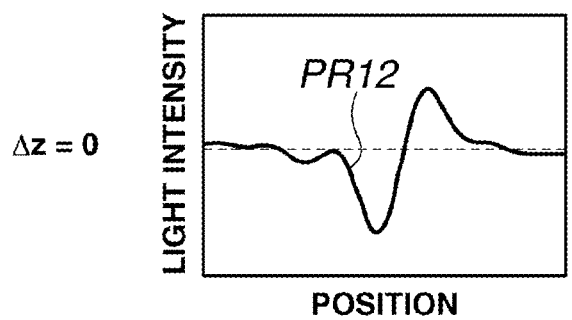
Figure 10D:
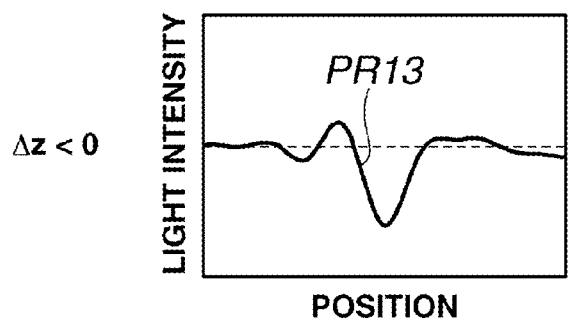

When the bump defect DEF9 and the pit defect DEF8 are subjected to irradiation of the surface of the photomask blank with inspection light from a left side in the figure by oblique illumination and the reflected light is collected by use of the inspecting optical system depicted in FIG. 4 like in the case of the pit defect depicted in FIGS. 5A and 5B and the bump defect depicted in FIGS. 6A and 6B, there is no difference in positional relation of the bright and dark portions between a sectional profile PR12 (FIG. 10C) of light intensity distribution of the bump defect DEF9 and the sectional profile PR7 (FIG. 8F) of light intensity distribution of the pit defect DEF8 in the focus condition ($\Delta z=0$), between a sectional profile PR11 (FIG. 10B) of light intensity distribution of the bump defect DEF9 and the sectional profile PR5 (FIG. 8D) of light intensity distribution of the pit defect DEF8 in the positive defocus condition ($\Delta z>0$), and between a sectional profile PR13 (FIG. 10D) of light intensity distribution of the bump defect DEF9 and the sectional profile PR9 (FIG. 8H) of light intensity distribution of the pit defect DEF8 in the negative defocus condition ($\Delta z<0$). Therefore, a defect that is actually a bump defect but would be determined to be a pit defect in the focus condition cannot be distinguished by the same technique as in the aforementioned first mode.

However, in the positive defocus condition, a comparison between the light intensity distribution of the bump defect due to an adhered matter of a material substantially transparent to inspection light and the light intensity distribution of the true pit defect DEF8 depicts that the ratio of the difference (absolute value) between the light intensity of a defect-free region and the light intensity of the bright portion to the difference (absolute value) between the light intensity of the defect-free region and the light intensity of the dark potion (the ratio will hereinafter referred to as "bright-to-dark ratio") is higher for the bump defect DEF9 than for the true pit defect DEF8. Thus, in the case of the bump defect due to the adhered matter of a material substantially transparent to inspection light, the bright portion tends to be emphasized. The difference between the light intensity of the defect-free region and the light intensity of the bright portion and the difference between the light intensity of the defect-free region and the light intensity of the dark portion vary depending on the size of the bump defect, but a reference intensity obtained in a defect-free region sufficiently spaced apart from the bump defect is specified by the structure of the optical thin film of the photomask blank and is constant in the defect-free region. In addition, in regard of true pit defects of various sizes and depths, the light intensities of the bright portion and dark portion can be preliminarily grasped in terms of bright-to-dark ratio values, by actual measurements or simulations. Therefore, when the light intensity of a defect-free region sufficiently spaced apart from the defect is used as a reference intensity and the light intensities of the bright portion and the dark portion are compared with the reference intensity, the following is possible. For example, when a predetermined threshold concerning the bright-to-dark ratio is preliminarily prescribed and a defect with a bright-to-dark ratio of up to the threshold (for example, up to 0.9) is determined to be a true pit defect whereas a defect with a bright-to-dark ratio exceeding the threshold is determined to be a bump defect, a defect that is actually a bump defect but would be determined to be a pit defect under the focus condition can be correctly determined to be a bump defect.

Besides, while an example of a defect present in an optical thin film of an MoSi material on a quartz substrate has been depicted in the above first mode and second mode, defects present in thin films such as other optical thin films and processing aid thin films to be used for photomask blanks, for example, thin films of chromium material, may also be objects of defect inspection by the defect inspecting method according to the present invention.

In the present invention, at the time of inspecting a defect present at a surface portion of a photomask blank having at least one thin film formed on a substrate, first, the rugged shape of the defect is determined in a focus condition by the following steps (A1) to (A3):

(A1) a step of bringing the defect and an objective lens of the inspecting optical system close to each other, setting a distance between the defect and the objective lens to a focus distance, and, with the focus distance thus set, applying inspection light to the defect through the objective lens;

(A2) a step of collecting reflected light from a region irradiated with the inspection light, through the objective lens, as a first magnified image of the region; and (A3) a first determination step of identifying a light intensity variation portion of the first magnified image and determining a rugged shape of the defect on the basis of a variation in light intensity of the light intensity variation portion of the first magnified image;

and the rugged shape of the defect is re-determined in a defocus condition by the following steps (B1) to (B3):

(B1) a step of setting the distance between the defect and the objective lens of the inspecting optical system to a defocus distance deviated from the focus distance, and, with the defocus distance thus set, applying the inspection light to the defect through the objective lens;

(B2) a step of collecting reflected light from a region irradiated with the inspection light, through the objective lens, as a second magnified image of the region; and (B3) a second determination step of identifying a light intensity variation portion of the second magnified image and re-determining the rugged shape of the defect on the basis of a variation in light intensity of the light intensity variation portion of the second magnified image.

By inspecting a defect by such a method as just-mentioned, it is possible to accurately determine the rugged shape of the defect without, for example, a problem that a defect that is actually a bump defect might be erroneously determined to be a pit defect.

In one or both of the step (A3) and the step (B3), the rugged shape of the defect to be inspected may be determined by comparison of a light intensity variation obtained by actually carrying out the above steps (B1) to (B3) for the pit defect or bump defect to be inspected, particularly, a true pit defect, with the light intensity variation of the first magnified image or the second magnified image. However, it is also possible to determine the rugged shape of the defect to be inspected, by comparison of a light intensity variation obtained by simulation for the pit defect or bump defect to be inspected, particularly, a true pit defect, with the light intensity variation of the first magnified image or the second magnified image. In this case, efficient determination can be achieved by obtaining a light intensity variation of particularly a true pit defect and determining a defect corresponding to this light intensity variation to be a pit defect while determining other defects to be bump defects.

In addition, when photomask blanks are produced by a method including a step of forming at least one thin film such as an optical thin film or a processing aid thin film on a substrate and a step of determining the rugged shape of a defect present in the thin film, it is possible to exclude those photomask blanks having a fatal defect, to select those photomask blanks having non-fatal defects such as removable defects or repairable defects, and to provide such fatal-defect-free photomask blanks as they are or after regenerating them.

Particularly, the present invention is effective, since when the steps (A1) to (A3) are carried out, and, if the defect shape is determined to be a recessed shape in the first determination step, the steps (B1) to (B3) are carried out to re-determine the rugged shape of the defect, it is possible to determine a defect that is actually a bump defect to be a projected shape, without erroneously determining the actually bump defect as a pit defect. In addition, by application of such a defect inspecting method, photomasks having no pit defects can be sort out from the photomask blanks subjected to the steps (B1) to (B3), on the basis of the rugged shape of the defects that is re-determined in the second determination step.

In the defect inspecting method of the present invention, the inspection light is preferably light having a wavelength of 210 nm to 550 nm. In addition, in one or both of the steps (A1) and (B1), the inspection light may be applied by oblique illumination in which the optical axis of the inspection light is oblique relative to the surface of the photomask blank. In one or both of the steps (A2) and (B2), a spatial filter for shielding part of the reflected light may be provided on the optical path of the reflected light, to collect the reflected light through the spatial filter. The defocus distance, which depends on the size and depth of the defect, is preferably in the range of −300 nm to +300 nm, more preferably −250 nm to +250 nm. In either of the ranges, 0 nm is excluded. Particularly, it is preferable to set the defocus distance to within a range excluding a range of more than −100 nm and less than +100 nm.

Further, in the step (A1), the photomask blank may be mounted on a stage that can be moved in an in-plane direction, and the stage may be moved in the in-plane direction to bring the defect and the objective lens of the inspecting optical system close to each other. When this configuration is adopted, easy positioning of the defect can be achieved. In addition, a continuous defect inspection can be carried out for a plurality of defects present on the photomask blank. Therefore, this configuration contributes to enhancement of efficiency.

Figure 11:
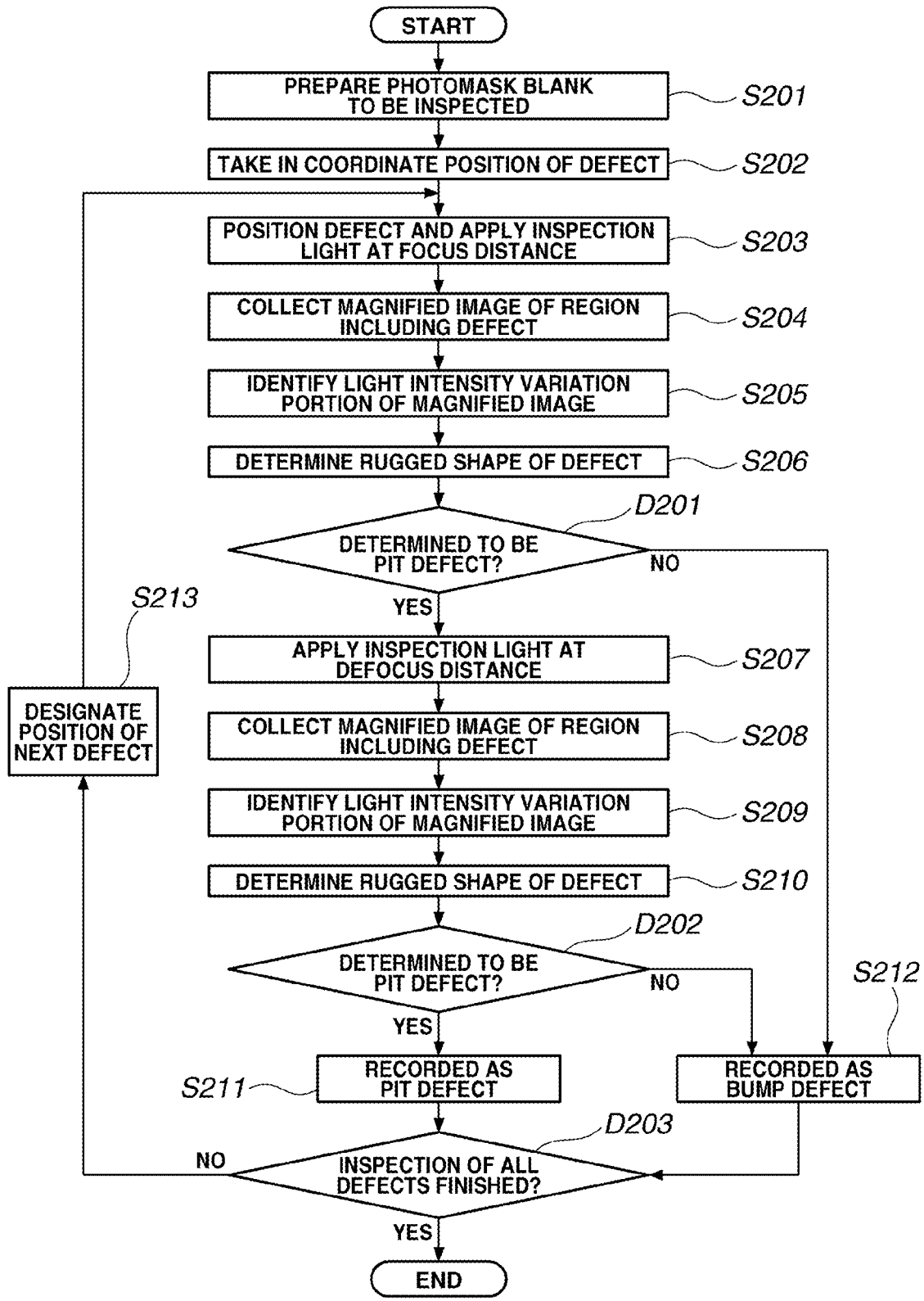
FIG. 11 is a flow chart of steps of a defect inspecting method.

In the next place, the defect inspecting method of the present invention will be described more specifically along a flow chart depicted in FIG. 11.

First, a photomask blank as an inspection object that has a defect (photomask blank to be inspected) is prepared (step S201). Next, position coordinate information on a defect present on the photomask blank is taken in (step S202). As the position coordinates of the defect, position coordinates of the defect that are identified by known defect inspection can be used.

Subsequently, as the step (A1), the position of the defect is adjusted to an inspection position of the inspecting optical system. Specifically, the defect and the objective lens of the inspecting optical system are brought close to each other, the distance between the defect and the objective lens of the inspecting optical system is set to a focus distance, and, with the focus distance maintained, inspection light is applied from an oblique direction through the objective lens (step S203). The positioning may be carried out by a method in which the photomask blank as an inspection object is mounted on a stage movable in an in-plane direction, the stage is moved in the in-plane direction on the basis of the position coordinates of the defect of the photomask blank as the inspection object, thereby bringing the defect and the objective lens of the inspecting optical system close to each other. Next, as the step (A2), the reflected light from a region irradiated with the inspection light is collected through the objective lens of the inspecting optical system as a first magnified image of the region including the defect (step S204). Subsequently, as the step (A3), a light intensity variation portion of the inspection image of the defect portion is identified from image data (inspection image) of the thus collected first magnified image (step S205), and, using the inspection light incidence side as a reference, the first determination step of determining the rugged shape of the defect portion from the positional relation of a bright portion and a dark portion of the inspection image is carried out (step S206).

Here, in the step S206, when the defect is not determined to be a pit defect, defect information is recorded as a bump defect (decision D201 and step S212).

On the other hand, when the defect is determined to be a pit defect in the step S206, as the step (B1), the distance between the defect and the objective lens of the inspecting optical system is set to a distance (positive or negative defocus distance) different from the focus distance, and, with the defocus distance maintained, the inspection light is applied from an oblique direction through the objective lens (step S207). Next, as the step (B2), the reflected light from the region irradiated with the inspection light is collected through the objective lens of the inspecting optical system as a second magnified image of the region including the defect (step S208). Subsequently, as the step (B3), a light intensity variation portion of the inspection image at the defect portion is identified from the image data (inspection image) of the collected second magnified image (step S209), and the second determination step of determining the rugged shape of the defect portion is carried out (step S210). The second determination step is carried out from the positional relation of the bright portion and the dark portion of the inspection image while using the inspection light incidence side as a reference, in the case of the first mode. In the case of the second mode, on the other hand, the second determination step is carried out by comparison of the light intensities of the bright and dark portions with a reference intensity, while using the light intensity at a defect-free region sufficiently spaced apart from the defect as the reference intensity.

Here, when the defect in question is determined to be a pit defect in the step S210, defect information is recorded as a pit defect (decision D202 and step S211). Conversely, when the defect in question is not determined to be a pit defect, defect information is recorded as a bump defect (decision D202 and step S212). Next, it is determined whether inspection of all the preliminarily designated defects has been finished (decision D203). When the inspection has not yet been finished, the position of a new defect is designated (step S213), the step returns to the step S203, then the steps (A1) to (A3) and further the steps (B1) to (B3) are repeated. When it is decided that the inspection of all the preliminarily designated defects has been finished (decision D203), the defect inspection is ended.

Figure 12:
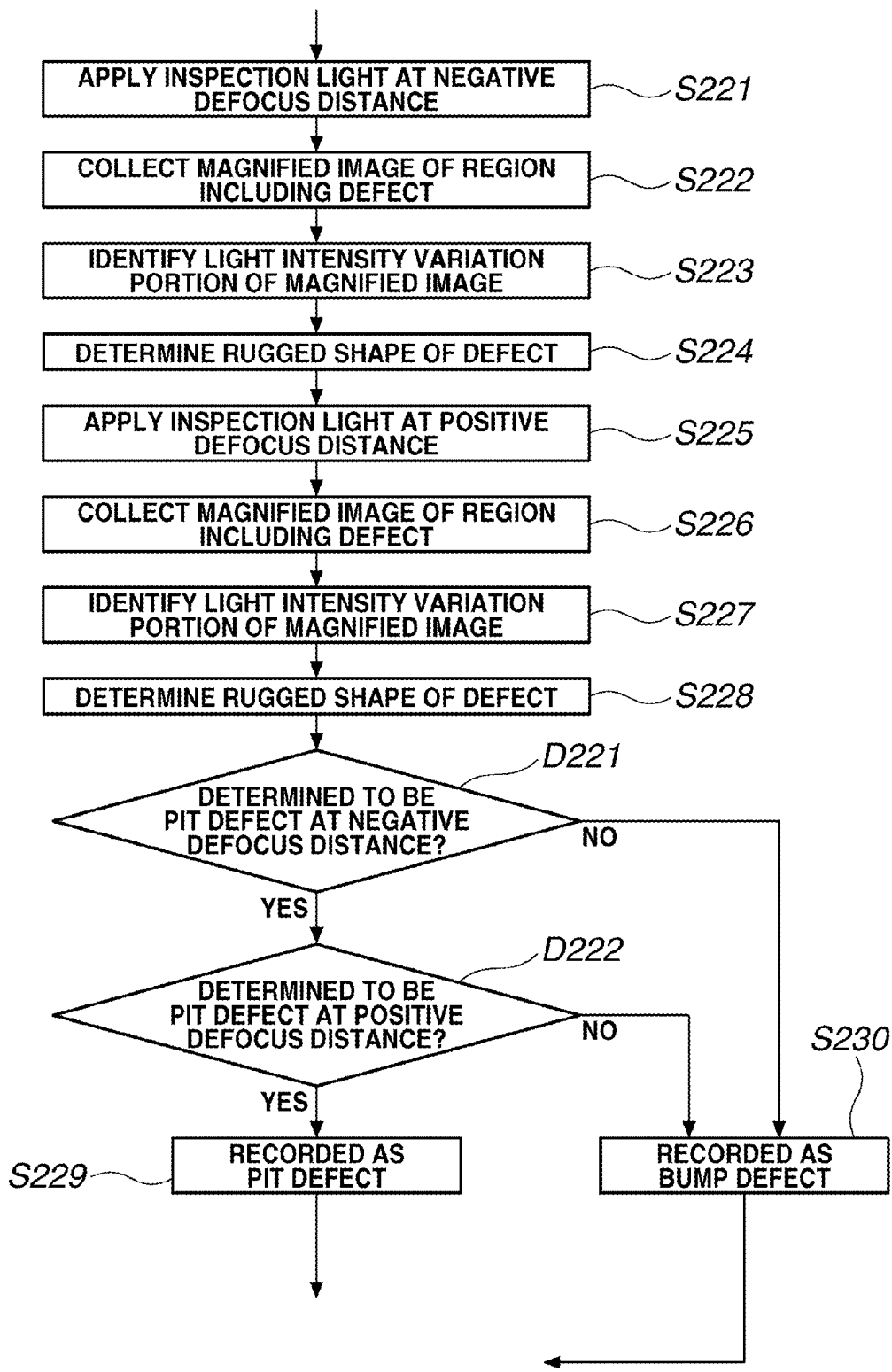
FIG. 12 is a flow chart of the steps of the defect inspecting method.

In the next place, an example of inspecting by a series of steps a bump defect due to a foreign matter of a material having a low refractive index (first mode) and a bump defect due to an adhered matter of a material substantially transparent to inspection light (second mode) will be described along a flow chart depicted in FIG. 12. In this case, in the flow chart depicted in FIG. 11, the steps S207 to S210 corresponding to the steps (B1) to (B3) and the subsequent decision D202 and steps S211 and S212 are replaced by the following.

When the defect in question is determined to be a pit defect in the step S206, first, as the step (B1), the distance between the defect and the objective lens of the inspecting optical system is set to a negative defocus distance different from the focus distance, and, with the negative defocus distance maintained, inspection light is applied from an oblique direction through the objective lens (step S221). Next, as the step (B2), the reflected light from the region irradiated with the inspection light is collected through the objective lens of the inspecting optical system as a second magnified image of the region including the defect (step S222). Subsequently, as the step (B3), a light intensity variation portion of an inspection image of the defect portion is identified on the basis of the image data (inspection image) of the thus collected second magnified image (step S223), and a second determination step of determining the rugged shape of the defect portion on the basis of the positional relation of a bright portion and a dark portion of the inspection image while using the inspection light incidence side as a reference is carried out (step S224).

Next, the distance between the defect and the objective lens of the inspecting optical system is set to a positive defocus distance different from the focus distance, and, with the positive defocus distance maintained, inspection light is applied from an oblique direction through the objective lens (step S225). Subsequently, as the step (B2), the reflected light from the region irradiated with the inspection light is collected through the objective lens of the inspecting optical system as a second magnified image of the region including the defect (step S226). Next, as the step (B3), a light intensity variation portion of the inspection image at the defect portion is identified on the basis of the image data (inspection image) of the thus collected second magnified image (step S227), and a second determination step of determining the rugged shape of the defect portion by comparison of light intensity of a bright portion or dark portion with a reference intensity while using the light intensity at a defect-free region sufficiently spaced apart from the defect as the reference intensity is carried out (step S228).

Here, in the step S224, when the defect in question is not determined to be a pit defect, defect information is recorded as a bump defect of the first mode (decision D221 and step S230). Conversely, when the defect in question is determined to be a pit defect, the step proceeds to determination result in the step S228. Then, when the defect in question is determined to be a pit defect in the step S228, defect information is recorded as a true pit defect (decision D222 and step S229), whereas when the defect in question is not determined to be a pit defect, defect information is recorded as a bump defect of the second mode (decision D222 and step S230). Note that the series of steps may be changed in their order within such a range that a reasonable flow can be realized. For example, the steps S221 to S224 to be carried out at a negative defocus distance may be conducted after the steps S225 to S228 to be carried out at a positive defocus distance is conducted. Besides, the steps to be carried out at a negative defocus distance and the steps to be carried out at a positive defocus distance may be performed alternately.

Where the defect inspecting method of the present invention by which the rugged shape of a defect can be discriminated highly reliably without erroneously determining a bump defect to be a pit defect is applied to a photomask blank production step, photomask blanks having a pit defect, particularly, a pinhole defect can be extracted highly reliably, and photomask blanks having no pinhole defect can be sorted out. In addition, information on the rugged shape of a defect obtained by the defect evaluation method of the present invention can be imparted to a photomask blank by accompaniment of an inspection card, for example. Further, the photomask blanks having no pit defect such as pinhole can also be sorted out on the basis of the information imparted to the photomask blanks. Conventionally, a bump defect due to an adhered matter might be determined to be a pit defect by optical inspection, and there has been a high possibility that a photomask blank having a defect that is not necessarily a fatal defect might be rejected as a defective, thus it leads to a lowering in the yield. By the inspecting method of the present invention, on the other hand, photomask blanks having a pit defect that is a fatal defect and present in a photomask blank can be rejected selectively, and, therefore, photomask blanks conforming to product specifications can be provided in a high yield.

EXAMPLES

The present invention will be described specifically below, referring to Examples, however the present invention is not to be limited to the following Examples.

Example 1

Figure 13A:
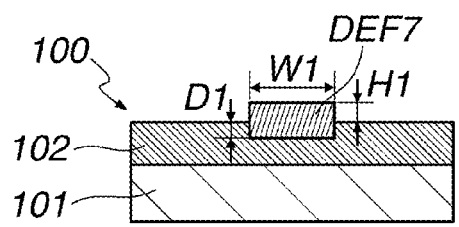
FIG. 13A is a sectional view of a photomask blank having a bump defect of Example 1.
Figure 14A:
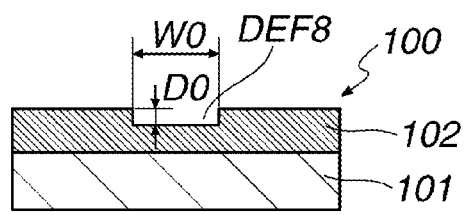
FIG. 14A is a sectional view of a photomask blank having a true pit defect as an object of comparison.

A defect inspection of a photomask blank having a bump defect of the first mode was carried out. The inspecting optical system depicted in FIG. 4 was used as an inspecting optical system, with a numerical aperture NA set to 0.75 and an inspection wavelength set to 248 nm. Oblique illumination was adopted in which inspection light is applied to the defect on the photomask blank from a left upper side in the figure at an average incidence angle of 38 degrees. A bump defect DEF7 due to a foreign matter of a material with a low refractive index that is formed on a surface portion of an optical thin film 102 of an MoSi material formed on a quartz substrate 101 transparent to the inspection light, as depicted in FIG. 13A, was used as an inspection object. For the inspection object, an inspection image representing light intensity distribution and a light intensity profile as to a section of the inspection object were obtained. In addition, a true pit defect DEF8 present at a surface portion of an optical thin film 102 of an MoSi material formed on a quartz substrate 101 transparent to inspection light, as depicted in FIG. 14A, was used as a comparative inspection object. For the comparative inspection object, an inspection image of light intensity distribution and a sectional profile of light intensity were obtained.

Figure 13B:
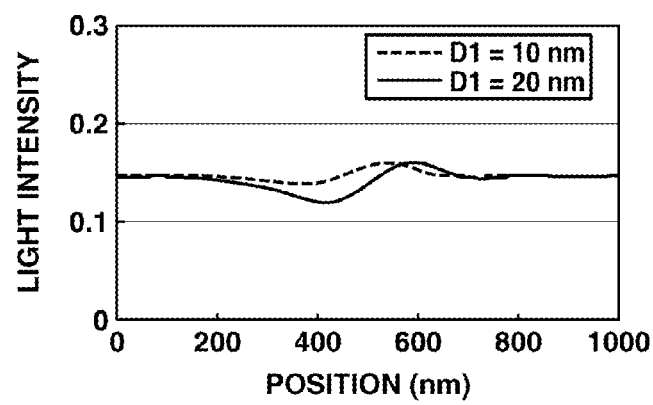
FIGS. 13B to 13D depict sectional profiles of light intensity distribution of inspection images of the bump defect in a positive defocus condition, a focus condition, and a negative defocus condition, respectively.
Figure 13C:
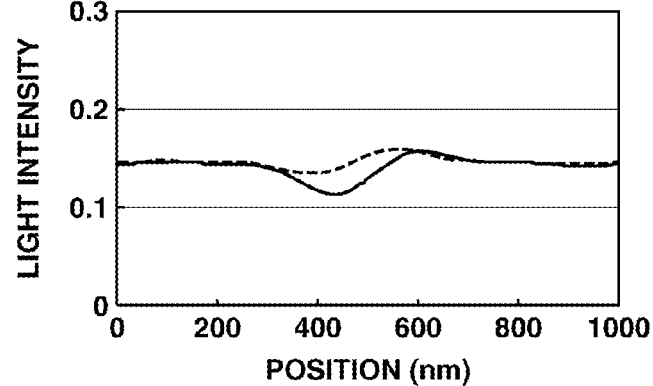
Figure 13D:
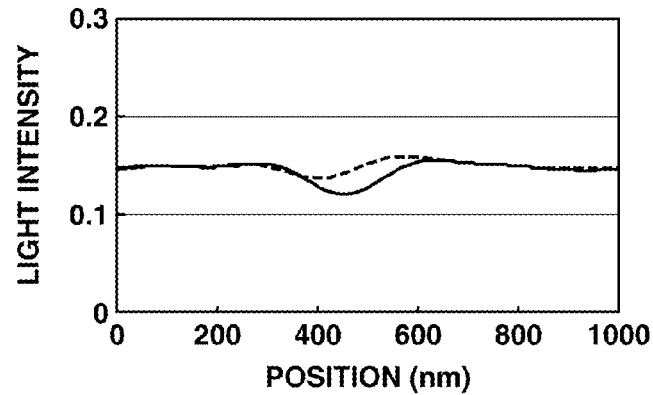

The bump defect DEF7 had a structure wherein a height H1 of a projected portion of the defect is 10 nm, a width W1 of the defect is 100 nm, and an embedded depth D1 of the defect is either of two values of 10 nm and 20 nm. FIG. 13B depicts a sectional profile of light intensity when the defocus distance was set to a positive value of +200 nm, FIG. 13C depicts a sectional profile of light intensity when the focus distance, or a focused condition, was set, and FIG. 13D depicts a sectional profile of light intensity when the defocus distance was set to a negative value of −200 nm.

Figure 14B:
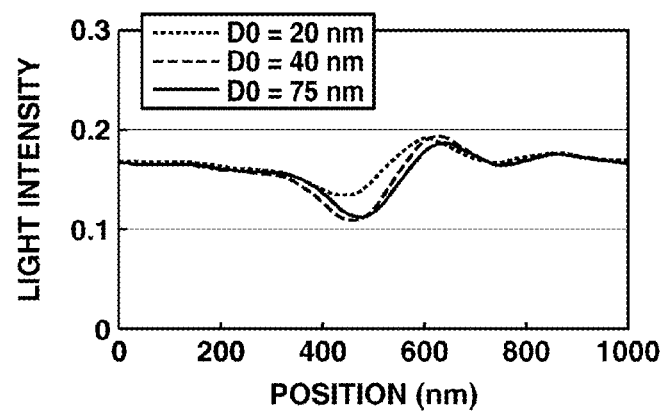
FIGS. 14B to 14D depict sectional profiles of light intensity distribution of inspection images of the true pit defect in a positive defocus condition, a focus condition, and a negative defocus condition, respectively.
Figure 14C:
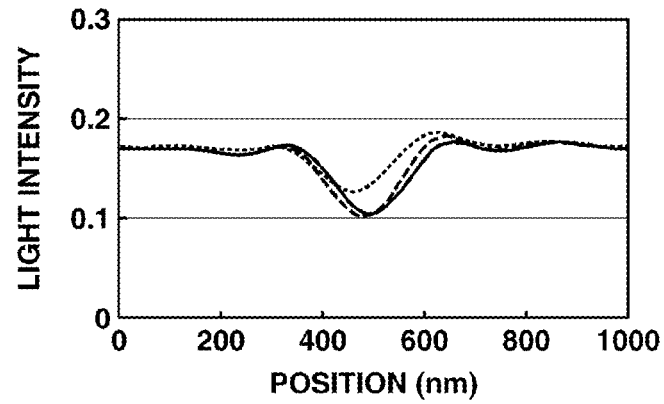
Figure 14D:
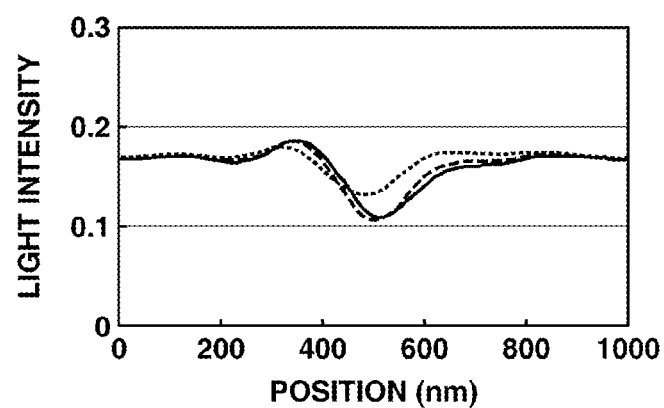

On the other hand, the true pit defect DEF8 had a structure wherein a width W0 of the defect is 100 nm. In consideration of the fact that a variation amount in light intensity of an inspection image varies depending on a depth D0 of the defect, the depth D0 was set to one of three values of 20 nm, 40 nm, and 75 nm. FIG. 14B depicts a sectional profile of light intensity when the defocus distance was set to a positive value of +200 nm, FIG. 14C depicts a sectional profile of light intensity when the focus distance, or a focused condition, was set, and FIG. 14D depicts a sectional profile of light intensity when the defocus distance was set to a negative value of −200 nm.

In the case of the focus distance ($\Delta z=0$ nm), or focused condition, the distribution (sectional profile of light intensity) of the inspection image of the true pit defect DEF8 has a dark portion on the left side and a bright portion on the right side; also, the distribution of the inspection image of the bump defect DEF7 has a dark portion on the left side and a bright portion on the right side. In this case, therefore, both the defects cannot be distinguished from each other. Similarly, in the case of the positive defocus distance ($\Delta z=+200$ nm), both the defects give a dark portion on the left side and a bright portion on the right side. On the other hand, in the case of the negative defocus distance ($\Delta z=-200$ nm), the bump defect DEF7 gives a dark portion on the left side and a bright portion on the right side, whereas the true pit defect DEF8 gives a bright portion on the left side and a dark portion on the right side; thus, there is an inversion of the positional relation of the bright and dark portions.

From these results it is seen that when the positional relation of the bright and dark portions is compared on the basis of inspection images obtained under the negative defocus condition, an embedded-type bump defect that would be determined to be a pit defect in the related-art inspection under the focused condition can be correctly determined to be a bump defect.

Example 2

Figure 15A:
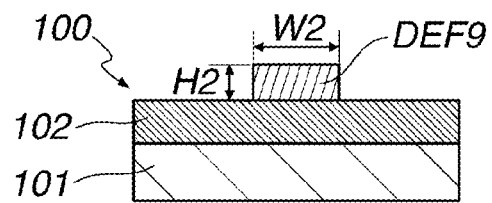
FIG. 15A is a sectional view of a photomask blank having a bump defect of Example 2.

Defect inspection of a photomask blank having a bump defect of the second mode was carried out. The inspecting optical system depicted in FIG. 4 was used as an inspecting optical system, with a numerical aperture NA set to 0.75 and an inspection wavelength set to 248 nm. Oblique illumination was adopted in which inspection light was applied to the defect on the photomask blank from a left upper side in the figure at an average incidence angle of 38 degrees. A bump defect DEF9 due to an adhered matter of a material substantially transparent to the inspection light that is present at a surface portion of an optical thin film 102 of an MoSi material formed on a quartz substrate 101 transparent to the inspection light, as depicted in FIG. 15A, was used as is an inspection object. For the inspection object, an inspection image representing light intensity distribution and a light intensity profile as to the section of the inspection object were obtained.

Figure 15B:
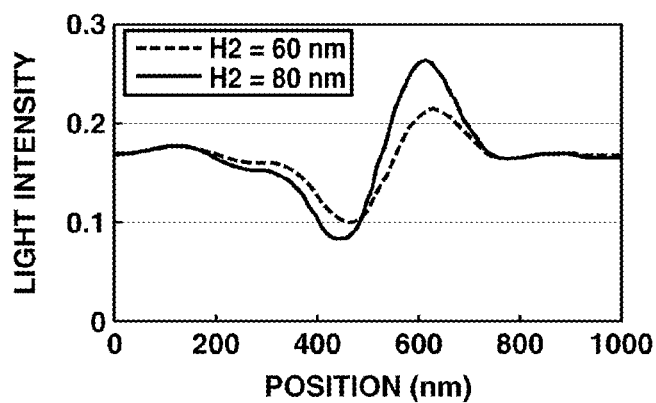
FIGS. 15B to 15D depict sectional profiles of light intensity distribution of inspection images of the bump defect in a positive defocus condition, a focus condition, and a negative defocus condition, respectively.
Figure 15C:
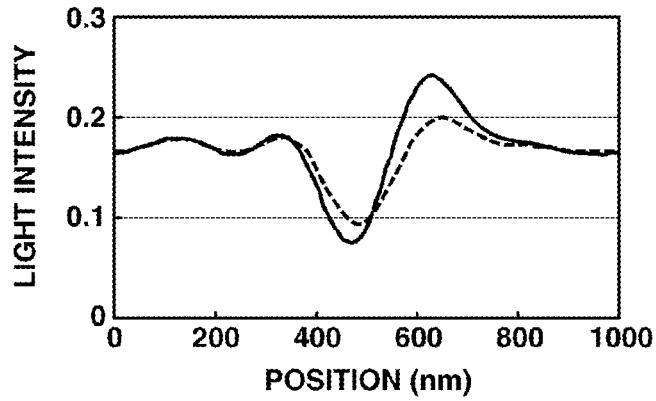
Figure 15D:
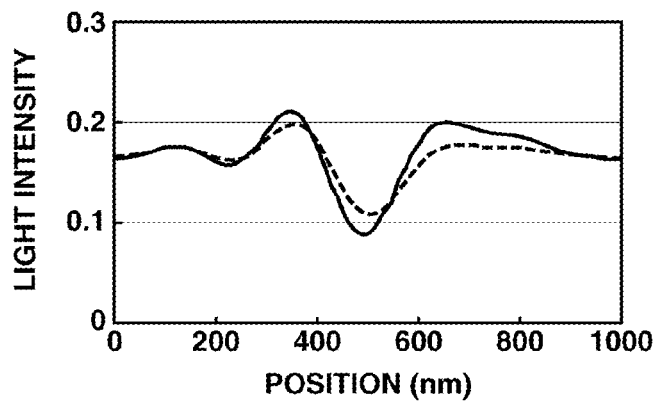

The bump defect DEF9 had a structure in which a height H2 of the defect is either one of two values of 60 nm and 80 nm and a width W2 of the defect is 100 nm. FIG. 15B depicts a sectional profile of light intensity when the defocus distance was a positive value of +200 nm, FIG. 15C depicts a sectional profile of light intensity when the focus distance, or a focused condition, was set, and FIG. 15D depicts a sectional profile of light intensity when the defocus distance was set to a negative value of −200 nm. On the other hand, the sectional profiles of light intensity relevant to a true pit defect DEF8, as depicted in FIG. 14A, used as a comparative inspection object, were as depicted in FIGS. 14B to 14D.

In the case of the focus distance ($\Delta z=0$ nm), or focused condition, and in the case of the positive defocus distance ($\Delta z=+200$ nm), both the defects give a dark portion on the left side and a bright portion on the right side. Also, in the case of the negative defocus distance ($\Delta z=-200$ nm), both the defects give a bright portion on the left side and a dark portion on the right side. Therefore, both the defects cannot be distinguished from each other by the positional relation of the bright and dark portions. Under the positive defocus condition, however, the light intensity level of the bright portion of the inspection image relevant to the bump defect DEF9 is definitely higher than that relevant to the true pit defect DEF8.

As a result of a detailed evaluation of these light intensity levels, the light intensity at a defect-free position sufficiently spaced apart from the defect (this light intensity serves as a reference intensity) was found to be 0.166. In this connection, in the case of the bump defect DEF9 with the height H2 of 80 nm, the variation amount in light intensity at the bright portion from the reference intensity was 0.076 under the focus condition, but was increased to 0.095 under the positive defocus condition. On the other hand, the variation amount in light intensity at the dark portion from the reference intensity was 0.089 under the focus condition, and was slightly decreased to 0.084 under the positive defocus condition. In other words, the bright-to-dark ratio under the focus condition is 0.85, whereas the bright-to-dark ratio under the positive defocus condition is 1.13. In the case of the positive defocus condition, the average light intensity level of the inspection image was raised, and the variation amount at the bright portion from the reference intensity was more than the variation amount at the dark portion from the reference intensity. In addition, in the case of the bump defect DEF9 with the height H2 of 60 nm, the variation amounts at the bright portion and the dark portion from the reference intensity were substantially the same level (that is, the bright-to-dark ratio was almost one).

On the other hand, for the true pit defect DEF8, even in the case of the depth D0 of 20 nm where the average light intensity level of the inspection image is the highest, the variation amount in light intensity at the bright portion from the reference intensity was 0.024 and the variation amount in light intensity at the dark portion from the reference intensity was 0.031 under the positive defocus condition; thus, the bright-to-dark ratio was 0.77, which was less than the bright-to-dark ratio for the bump defect DEF9. In addition, for the true pit defect DEF8 with the depth D0 being deeper levels of 40 nm or 75 nm, the average light intensity level of the inspection image was lower than this, and the bright-to-dark ratio was further lowered.

From these results it is seen that when the ratio of the difference (absolute value) between the light intensity at the defect-free region and the light intensity at the bright portion to the difference (absolute value) between the light intensity at the defect-free region and the light intensity at the dark portion, or the bright-to-dark ratio, is compared with the bright-to-dark ratio of the true pit defect DEF8 under the positive defocus condition, an adhered matter type bump defect that would be determined to be a pit defect in the related-art inspection under the focus condition can be correctly determined to be a bump defect.

Japanese Patent Application No. 2015-129006 , is incorporated herein by reference.

Although some preferred examples have been described, many modifications and variations may be made thereto in light of the above teachings. It is therefore to be understood that the invention may be practiced otherwise than as specifically described without departing from the scope of the appended claims.

The invention claimed is:

1. A method of inspecting a defect present at a surface portion of a photomask blank comprising at least one thin film formed on a substrate, by use of an inspecting optical system, the method comprising:
(A1) a step of bringing the defect and an objective lens of the inspecting optical system close to each other, setting a distance between the defect and the objective lens to a focus distance, and, with the focus distance thus set, applying inspection light to the defect through the objective lens;
(A2) a step of collecting reflected light from a region irradiated with the inspection light, through the objective lens, as a first magnified image of the region;
(A3) a first determination step of identifying a light intensity variation portion of the first magnified image and determining a rugged shape of the defect on the basis of a variation in light intensity of the light intensity variation portion of the first magnified image;
(B1) a step of setting the distance between the defect and the objective lens of the inspecting optical system to a defocus distance deviated from the focus distance, and, with the defocus distance thus set, applying the inspection light to the defect through the objective lens;
(B2) a step of collecting reflected light from a region irradiated with the inspection light, through the objective lens, as a second magnified image of the region; and
(B3) a second determination step of identifying a light intensity variation portion of the second magnified image and re-determining the rugged shape of the defect on the basis of a variation in light intensity of the light intensity variation portion of the second magnified image, wherein
when defect shape is determined to be a recessed shape in the first determination step, the steps (B1) to (B3) are carried out to re-determine the rugged shape of the defect.

2. The method of inspecting a defect according to claim 1, wherein in the step (B3), the rugged shape of the defect to be inspected is re-determined by comparison between a light intensity variation of a light intensity variation portion of a true pit defect that is preliminarily obtained by simulation and the light intensity variation of the light intensity variation portion of the second magnified image.

3. The method of inspecting a defect according to claim 1, wherein the inspection light is light having a wavelength of 210 nm to 550 nm.

4. The method of inspecting a defect according to claim 1, wherein in both the step (A1) and the step (B1), application of the inspection light is conducted by oblique illumination in which optical axis of the inspection light is oblique in relation to a surface of the photomask blank.

5. The method of inspecting a defect according to claim 1, wherein in both the step (A2) and the step (B2), a spatial filter for shielding part of the reflected light is provided on an optical path of the reflected light, and the reflected light is collected through the spatial filter.

6. The method of inspecting a defect according to claim 1, wherein in the step (A1), the photomask blank is placed on a stage that can be moved in an in-plane direction of the photomask blank, and the stage is moved in the in-plane direction to thereby bring the defect and the objective lens of the inspecting optical system close to each other.

7. A method of sorting a photomask blank, comprising sorting out a photomask blank having no pit defect from the photomask blanks subjected to the steps (B1) to (B3), on the basis of the rugged shape of the defect re-determined in the second determination step of the method of inspecting a defect according to claim 1.

8. A method of producing a photomask blank, comprising:
a step of forming at least one thin film on a substrate; and
a step of determining rugged shape of a defect present in the thin film by the method of inspecting a defect according to claim 1.

9. A method of inspecting a defect present at a surface portion of a photomask blank comprising at least one thin film formed on a substrate, by use of an inspecting optical system, the method comprising:
(A1) a step of bringing the defect and an objective lens of the inspecting optical system close to each other, setting a distance between the defect and the objective lens to a focus distance, and, with the focus distance thus set, applying inspection light to the defect through the objective lens;
(A2) a step of collecting reflected light from a region irradiated with the inspection light, through the objective lens, as a first magnified image of the region;
(A3) a first determination step of identifying a light intensity variation portion of the first magnified image and determining a rugged shape of the defect on the basis of a variation in light intensity of the light intensity variation portion of the first magnified image;
(B1) a step of setting the distance between the defect and the objective lens of the inspecting optical system to a defocus distance deviated from the focus distance, and, with the defocus distance thus set, applying the inspection light to the defect through the objective lens;

(B2) a step of collecting reflected light from a region irradiated with the inspection light, through the objective lens, as a second magnified image of the region; and (B3) a second determination step of identifying a light intensity variation portion of the second magnified image and re-determining the rugged shape of the defect on the basis of a variation in light intensity of the light intensity variation portion of the second magnified image, wherein the inspection light is light having a wavelength of 210 nm to 550 nm.

10. The method of inspecting a defect according to claim 9, wherein in the step (B3), the rugged shape of the defect to be inspected is re-determined by comparison between a light intensity variation of a light intensity variation portion of a true pit defect that is preliminarily obtained by simulation and the light intensity variation of the light intensity variation portion of the second magnified image.

11. The method of inspecting a defect according to claim 9, wherein in both the step (A1) and the step (B1), application of the inspection light is conducted by oblique illumination in which optical axis of the inspection light is oblique in relation to a surface of the photomask blank.

12. The method of inspecting a defect according to claim 9, wherein in both the step (A2) and the step (B2), a spatial filter for shielding part of the reflected light is provided on an optical path of the reflected light, and the reflected light is collected through the spatial filter.

13. The method of inspecting a defect according to claim 9, wherein in the step (A1), the photomask blank is placed on a stage that can be moved in an in-plane direction of the photomask blank, and the stage is moved in the in-plane direction to thereby bring the defect and the objective lens of the inspecting optical system close to each other.

14. A method of sorting a photomask blank, comprising sorting out a photomask blank having no pit defect from the photomask blanks subjected to the steps (B1) to (B3), on the basis of the rugged shape of the defect re-determined in the second determination step of the method of inspecting a defect according to claim 9.

15. A method of producing a photomask blank, comprising:

a step of forming at least one thin film on a substrate; and a step of determining rugged shape of a defect present in the thin film by the method of inspecting a defect according to claim 9.

* * * * *